US00PP23669P3

(12) United States Plant Patent
Goffreda et al.

(10) Patent No.: US PP23,669 P3
(45) Date of Patent: Jun. 18, 2013

(54) PEACH TREE NAMED 'NJ354'

(50) Latin Name: ***Prunus persica* L.**
Varietal Denomination: NJ354

(75) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 11 days.

(21) Appl. No.: 13/200,085

(22) Filed: Sep. 16, 2011

(65) Prior Publication Data

US 2013/0074227 P1 Mar. 21, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

*Primary Examiner* — Kent L Bell
(74) *Attorney, Agent, or Firm* — James A. Lucas; Driggs, Hogg, Daugherty & Del Zoppo Co., LPA

(57) ABSTRACT

A new and distinct peach variety of *Prunus persica* named 'NJ354' is provided. This variety is distinguished from other peach varieties by its unique combination of non showy flowers, large fruit that ripen in early-season, with an attractive red over color, clingstone fruit with a juicy, but firm melting texture and sweet, low acidic flavor, and excellent production of firm fruit that maintain their eating quality following cold storage.

6 Drawing Sheets

Latin name of genus and species of the plant claimed: *Prunus persica* L.

Variety denomination: 'NJ354'.

CROSS REFERENCE TO RELATED APLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of peach tree named 'NJ354'. Our new tree resulted from crossing as the seed parent with 'White Lady' peach tree, as the pollen parent. The new variety differs from seed parent NJ318 (unpatented) in that the new variety has firm fruit with a high percentage of red over color, while the seed parent has comparatively soft fruit that typically have a low percentage of red over color. The new variety differs from pollen parent 'White Lady' (U.S. Plant Pat. No. 5,821) in that the new variety ripens early, and has non-showy flowers, while the pollen parent ripens in mid-season and has showy flowers. In comparison to the commercial peach variety 'Sugar May' (U.S. Plant Pat. No. 8,034), the fruit of the new variety has a brighter red blush, is lower in acidity and matures approximately 5 days later. The fruit and leaves of the new variety are also more tolerant to bacterial leaf spot than 'Sugar May'. The resulting tree was selected when growing in a cultivated area as the $147^{th}$ tree in the $88^{th}$ row of Block D at a fruit research center located in Cream Ridge, N.J.

BRIEF SUMMARY OF THE INVENTION

The 'NJ354' variety is distinguished from other peach varieties due to the following unique combination of characteristics:

- Large round fruit with a low tendency to split for the season.
- Highly colored fruit with an attractive red over color.
- Excellent production of firm fruit that ripen in early-season.
- Sweet fruit with a good to very good eating quality.

The variety was asexually reproduced at the fruit research center in Cream Ridge, N.J. Asexual reproduction of this new variety by budding onto 'Lovell' rootstock (unpatented) shows that the foregoing characteristics are so reproduced.

The following detailed description concerns the original tree, 'NJ354'. The original tree and asexual progeny have been observed growing in a cultivated area at the fruit research center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to *The Royal Horticultural Society* (*R.H.S.*) *Colour Chart*. (1966 Edition).

BRIEF DESCRIPTION OF THE DRAWINGS

This new variety is illustrated by the accompanying photographic drawings, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
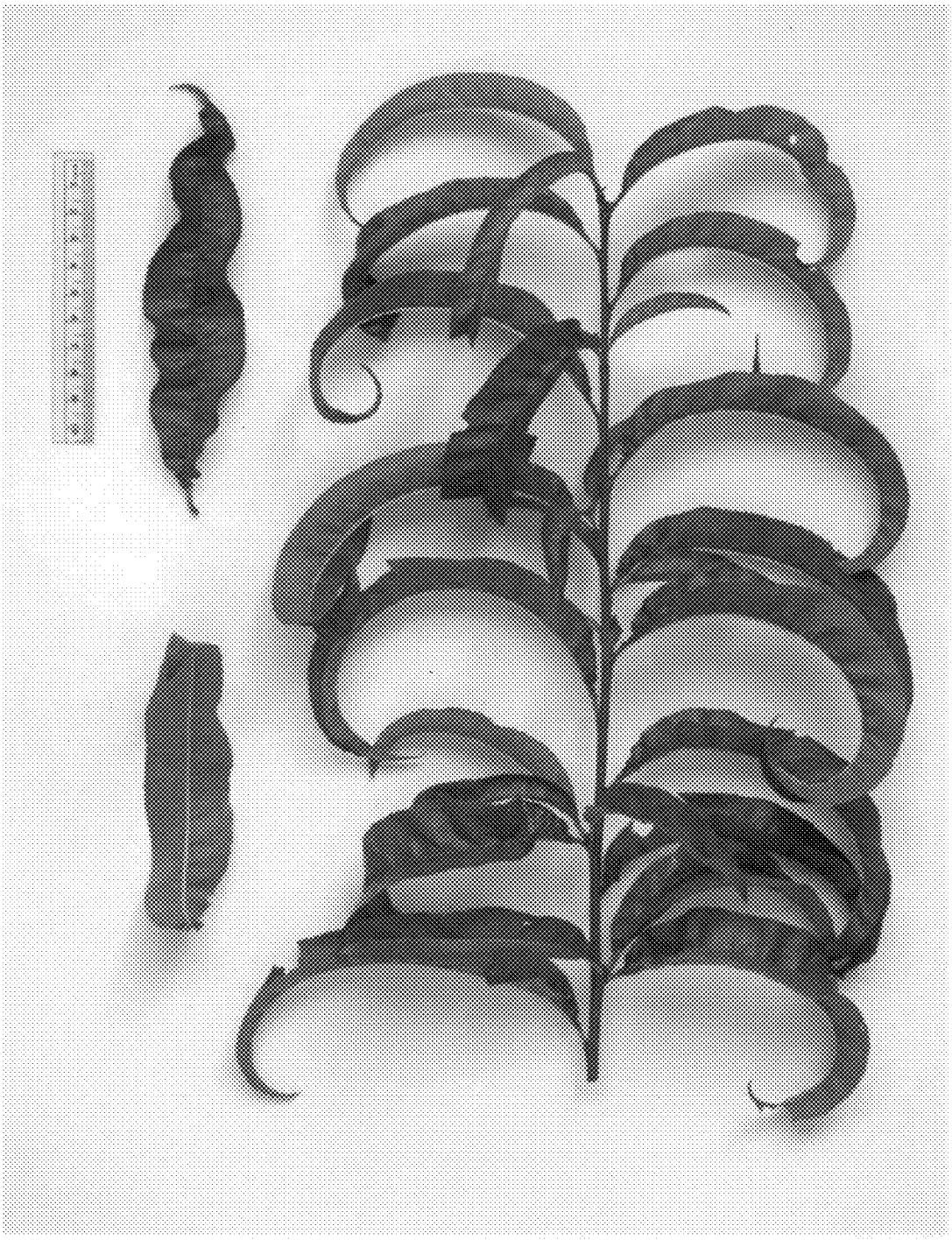
FIG. 1 is a color photograph taken on Aug. 25, 2005 of a characteristic twig of 'NJ354' in late summer bearing typical leaves of the mature foliage.
Figure 2:
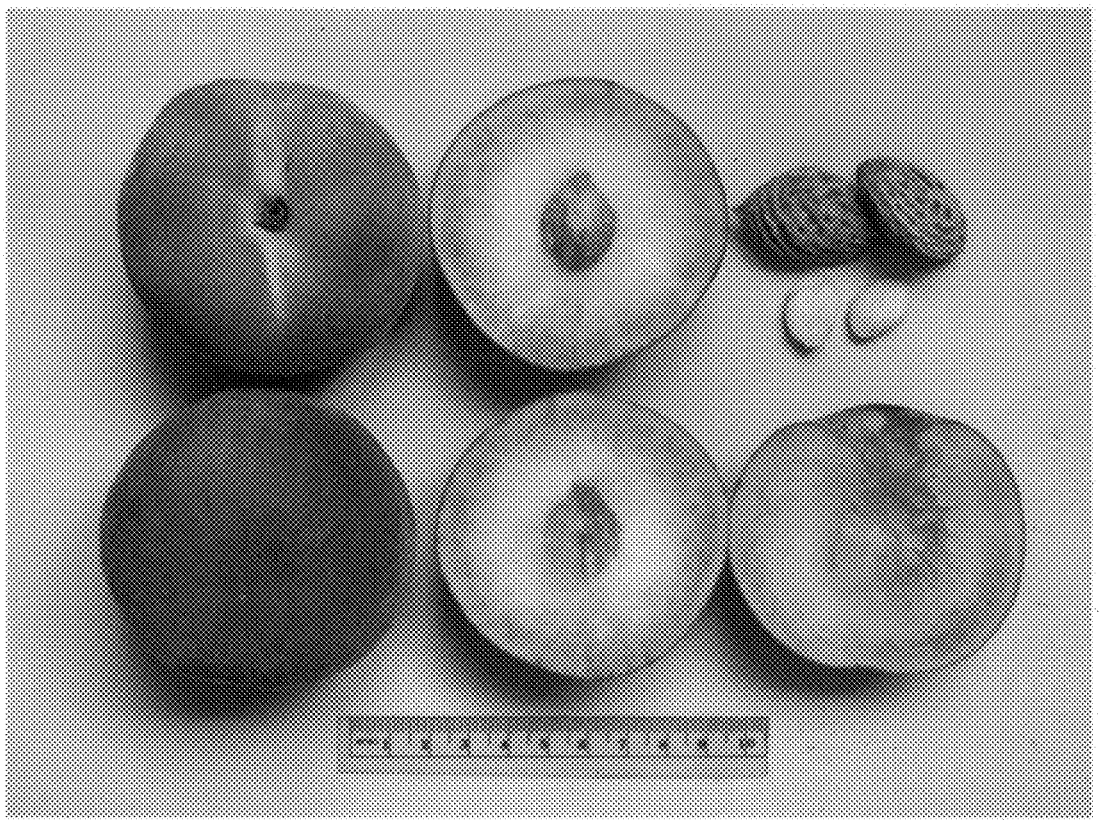
FIG. 2 is a color photograph taken on Jul. 27, 2005 of characteristic mature fruit and stones of 'NJ354'. Whole fruit are presented in two positions and transverse and longitudinal cross sections to show that the pericarp tends to adhere to the pit when the fruit is mature. The stones illustrate the obovoid shape and the pit grooves on the surface of the stone.
Figure 3:
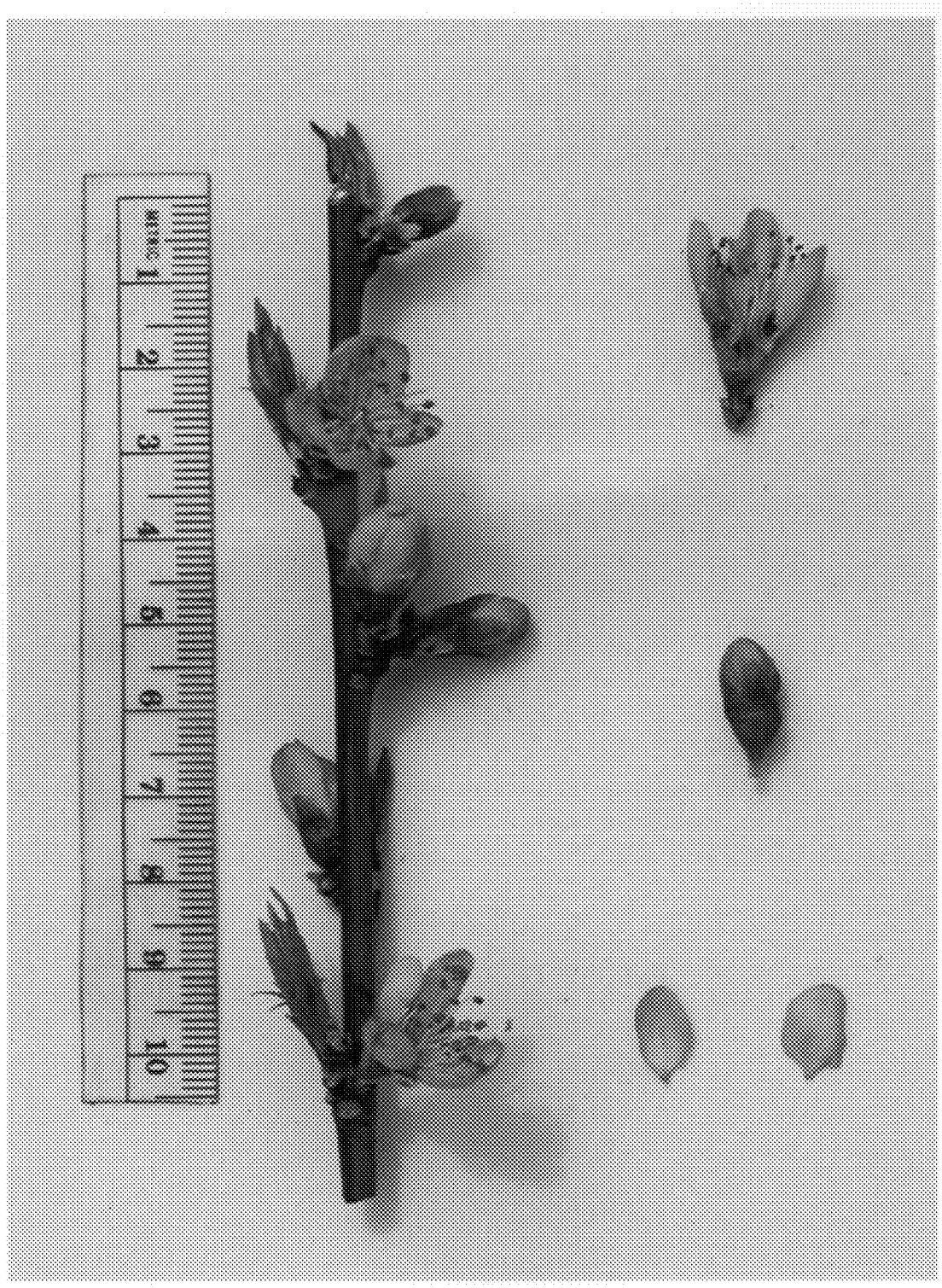
FIG. 3 is a color photograph taken on Apr. 21, 2004 of a characteristic twig that illustrates the typical flower buds and small, non-showy flowers of 'NJ354' observed on a tree that was 6 years of age.
Figure 4:
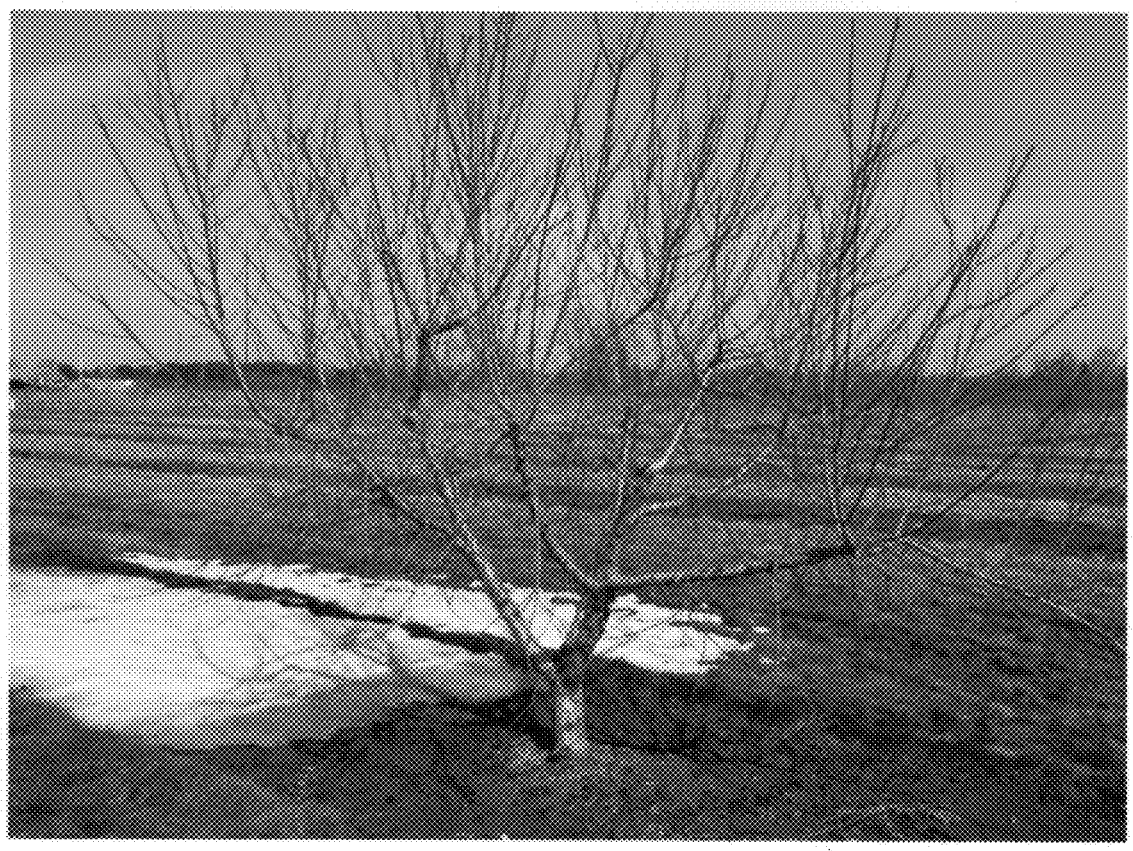
FIG. 4 is a color photograph of a dormant tree of 'NJ354' in late winter, prior to pruning, that illustrates the spreading growth habit of a tree on Feb. 17, 2011.
Figure 5:
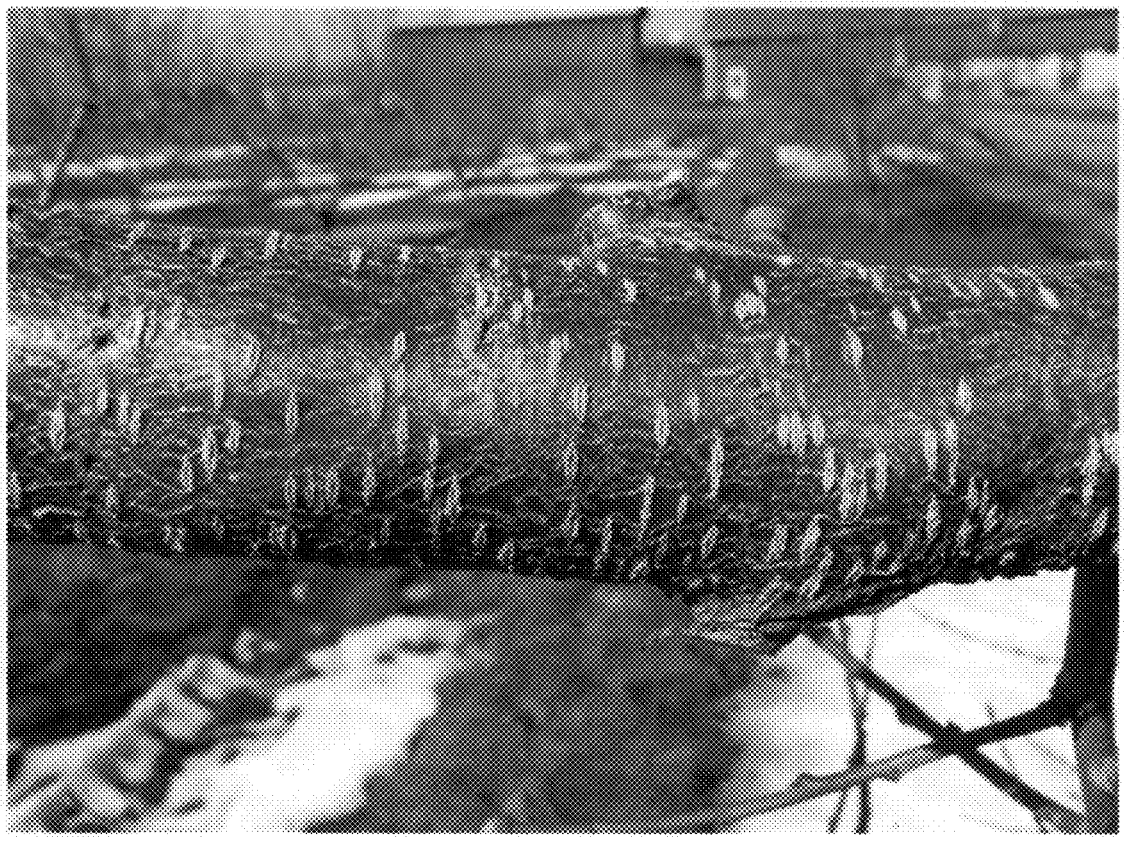
FIG. 5 is a color photograph taken on Feb. 17, 2011 of immature bark of 'NJ354' that illustrates color and the comparatively moderate density of conspicuous lenticels on the immature bark.
Figure 6:
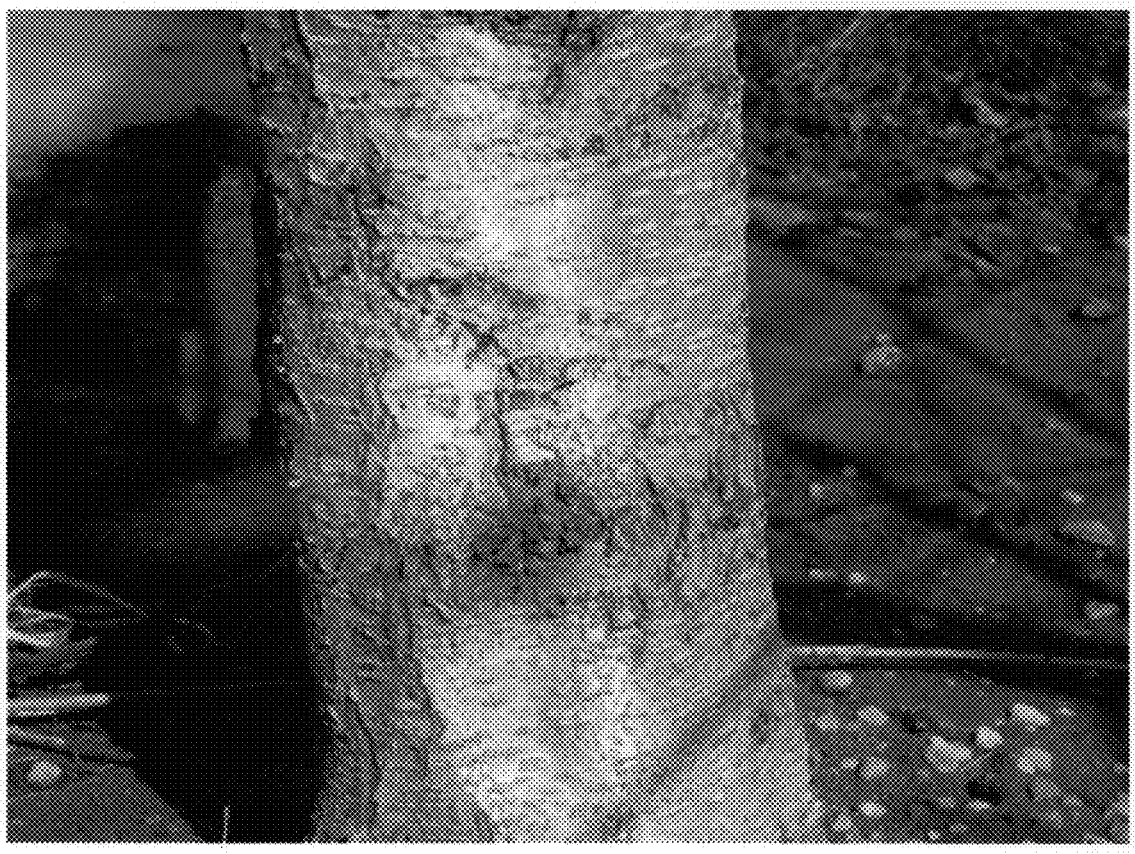
FIG. 6 is a color photograph taken on Feb. 17, 2011 of mature bark of 'NJ354' that illustrates the moderately rough texture of the mature bark.

The colors and illustration of this type may vary with lighting and other conditions and, therefore, color characteristics of this new variety should be determined with reference to the observations described herein, rather than from these illustrations alone.

DETAILED BOTANICAL DESCRIPTION

The following detailed description of the 'NJ354' variety is based on observations of an asexually reproduced tree. The observed tree was six years of age and growing on 'Lovell' seedling rootstock (unpatented) in Research Block E at the fruit research center in Cream Ridge, N.J.

Scientific name: *Prunus persica* L.

Parentage:

| | |
|---|---|
| Seed parent: | NJ318 |
| Pollen parent: | 'White Lady'. |

Tree:

| | |
|---|---|
| Vigor: | Moderately vigorous. |
| Plant hardiness zone: | Growth of plants has only been observed in zone 6b. |
| Dormant flower bud cold tolerance: | At least to −18° C. |
| Overall shape: | Spreading. |
| Height: | Average as compared to other peach cultivars. For example, measurement of a typical grafted tree on 'Lovell' seedling rootstock (unpatented) at six years after planting shows an average height of 3.4 meters when grown in Cream Ridge, New Jersey. |
| Width: | Slightly above average as compared to other peach cultivars. For example, measurement of a typical grafted tree on 'Lovell' seedling rootstock (unpatented) at six years after planting shows an average width of 4.6 meters when grown in Cream Ridge, New Jersey. |
| Caliper: | Six year old tree is 44 cm in circumference measured at 20 cm from the ground. |

Trunk and branches:

| | |
|---|---|
| Trunk bark texture: | Slightly rough, with few shallow fissures. |
| Trunk bark color: | Greyed-green (RHS 197D). |
| Primary branches: | Branches that are approximately 18 cm in circumference are greyed-orange (RHS 177B) in color, overlaid with greyed-green (RHS 198D). Branch angles range from 50 to 60 degrees, averaging about 53.4 degrees. |
| Lenticels: | Moderate density, approximately 1.9 per square cm; lanceolate in shape and relatively conspicuous; typical examples of which measured 4.0 mm in length and 0.9 mm in width; greyed-orange (between RHS 165C and RHS 165D) in color and bordered with greyed-brown (RHS 199D). |
| Branch pubescence: | None. |
| New growth bark: | Greyed-purple (RHS 183A) in sun; color yellow-green (between RHS 152B and RHS 152D) in shade. |
| Internodes: | Length averaging 19 mm on a one-year shoot. |

Leaves:

| | |
|---|---|
| Texture: | Glabrous. |
| Sheen: | Young leaves semi-glossy with a flat finish on the underside. Adaxial surface of mature leaves are generally smooth, glabrous, slightly glossy. Abaxial surface of mature leaves are nearly smooth, glabrous, with a matte finish. |
| Length: | About 176 mm to 188 mm, averaging about 181 mm including the petiole. |
| Width: | About 37 mm to 47 mm, averaging about 41 mm. |
| Petiole: | Averaging 19.8 mm long and about 1.8 mm in diameter. |
| Margin: | Serrulate. |
| Margin undulation: | Moderate. |
| Form: | Lanceolate. |
| Apex: | Sharply acute, and typically sharply curled downward. |
| Base: | Broadly acute. |
| Venation: | Pinnate. |
| Glands: | |
| Number: | About 2 to 6, averaging about 4.4. |
| Position: | Typically located on the leaf margin and petiole. |
| Size: | Length averaging 1.1 mm and width averaging 0.9 mm. |
| Form: | Reniform. |
| Stipules: | None observed on mature leaves. |
| Leaf Color: | |
| Upper leaf surface: | Yellow-green (between RHS 147A and RHS 147B). |
| Lower leaf surface: | Yellow-green (RHS 147B). |
| Vein: | Yellow-green (RHS 145C). |
| Pubescence: | None. |

Flowers:

| | |
|---|---|
| Size: | Small size, typical flower measuring between 15 mm to 19 mm, averaging about 18 mm across. |
| Color: | |
| Dormant bud: | Grey (RHS 201B) and greyed-green (RHS 196A). |
| Pink stage bud: | Red (between RHS 54A and RHS 55D). |
| Open flower: | Red (between RHS 62B and RHS 62C). |
| Petals: | Typically five petals per flower; cupped and elliptic in shape; margin entire, averaging about 12.9 mm long and 9.5 mm wide. |
| Petal apex: | Obtuse. |
| Petal base: | Cuneate. |
| Stamens: | |
| Number: | Variable, typical range 33 and 38, averaging 36.2. |
| Length: | Between 9.8 mm to 13 mm, averaging 11.9 mm. |

-continued

| | |
|---|---|
| Filament color: | Green-white (RHS 157C). |
| Anther color: | Red (RHS 46A). |
| Pistil: | |
| Number: | One. |
| Size: | Length between 15.2 and 18.9 mm, averaging about 17.2 mm. |
| Pistil color: | Yellow-green (between RHS 145A and RHS 145B). |
| Ovary: | Moderately pubescent and ellipsoid in shape. |
| Sepals: | |
| Number: | Five. |
| Pubescence: | Moderate length, and low to moderate density, increasing towards the edge. |
| Color: | Yellow-green (RHS 146D) with a greyed-red (RHS 176B) over color. |
| Shape: | Triangular, with a rounded apex. |
| Size: | Length averaging 5.5 mm, width averaging 4.2 mm. |
| Nectar cup color: | Between yellow (RHS 7A) and yellow-orange (RHS 15B). |
| Pollen: | Abundant; yellow-orange (RHS 16A) in color. |
| Fragrance: | Very slight. |
| Bloom season: | Onset of bloom in 2004 on April 17; full bloom on April 19. |

Fruit:

| | |
|---|---|
| Size: | Large, averaging about 6.8 cm long, 7.3 cm wide parallel to the suture and 7.3 cm wide perpendicular to the suture. |
| Typical weight: | Between 176 g and 238 g, averaging about 203 g. |
| Form: | |
| Longitudinal section: | Nearly round. |
| Traverse section: | Round. |
| Suture: | Very shallow, extending from the base to apex. |
| Ventral surface: | Typically smooth. |
| Base: | Flat. |
| Apex: | Flat. |
| Stem: | Average length of 4.6 mm and an average diameter of 3.3 mm. |
| Skin: | |
| Thickness: | Average. |
| Surface: | Glabrous, typically glossy. |
| Tenacity: | Average. |
| Astringency: | None. |
| Tendency to crack: | Low. |
| Color: | Slightly mottled red-purple (RHS 59A) over a red (RHS 46A) blush; ground color red (between RHS 49B and RHS 49D). |
| Fruit Properties: | |
| Flesh color: | Green-white (RHS 157D) flecked with red (between RHS 46A and RHS 46B), especially towards the skin. |
| Flesh adhesion: | Clingstone. |
| Juice: | Moderate. |
| Texture: | Firm, but melting. |

-continued

| | |
|---|---|
| Fibers: | Not noticeable. |
| Ripens: | Between July 14 and July 30 at Cream Ridge, New Jersey. |
| Flavor: | Above average, generally sweet with little acidity. |
| Soluble solids: | 10.9%. |
| Aroma: | Very slight. |
| Eating quality: | Good to very good. |
| Keeping quality: | Average. Has held its flavor and firmness for at least seven days in cold storage at 1° C to 4° C. |
| Shipping quality: | Very good. Fruit are generally very firm at harvest. No bruising or scaring disorders have been observed. |
| Usage: | Dessert. |
| Market: | Local and long distance. |
| Productivity: | Excellent. Trees have produced a crop in 10 out of 10 years and a full crop in 8 out of 10 years at Cream Ridge, New Jersey. |

Stone:

| | |
|---|---|
| Type: | Clingstone. |
| Form: | Obovoid |
| Base: | Narrow to medium. |
| Apex: | Narrow. |
| Surface: | Pit grooves. |
| Ventral suture: | Small. |
| Dorsal ridge: | Medium height, narrow width, forming fine lines. |
| External color: | Between orange-white (RHS 159A) and greyed-orange (RHS 165D). |
| Internal color when cracked: | Orange-white (RHS 159A). |
| Cavity surface color: | Greyed-orange (RHS 164C). |
| Average stone dry weight: | 4.55 g. |
| Average stone wall thickness: | Varies between 4.4 mm along ventral suture to 9.4 mm at the base. |
| Size: | Averages about 26.7 mm long, 21.9 mm wide parallel to the dorsal ridge, and 16.0 mm wide perpendicular to the dorsal ridge. |
| Tendency to split: | Low. |
| Kernel: | |
| Form: | Highly variable; forms only rudimentary seed. |
| Skin color: | Greyed-orange (between RHS 165A and RHS 165B). |
| Vein color: | Greyed-orange (between RHS 165A and RHS 165B). |
| Viability: | No. |
| Size: | Highly variable; forms only rudimentary seed with a dry weight of about 0.1 g. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *